United States Patent [19]

Bergeson

[11] Plant 4,904

[45] Oct. 26, 1982

[54] GREEN ASH TREE

[76] Inventor: Paul L. Bergeson, Rte. 1, Fertile, Minn. 56540

[21] Appl. No.: 161,648

[22] Filed: Jun. 20, 1980

[51] Int. Cl.[3] ..... A01H 5/00

[52] U.S. Cl. ..... Plt./51

[58] Field of Search ..... Plt./51

*Primary Examiner*—James R. Feyrer

*Attorney, Agent, or Firm*—Merchant, Gould, Smith, Edell, Welter & Schmidt

[57] ABSTRACT

A green ash tree which exhibits a rapid, straight, quick-branching, vigorous, upright, uniform and seedless growth habit which requires little or no pruning and produces a desirable nursery-grown tree for commercial sale in a minimum of growing time. The tree has narrow glossy green leaves, an attractive bronze bark color, a pronounced stronger caliper, a tendency to branch the first year of growth, and longer retention of leaves in autumn.

6 Drawing Figures

ORIGIN OF THE CULTIVAR

The present invention relates to a new and distinct variety of green ash tree which was discovered by me in 1976 in the cultivated nursery of my family, known as Bergeson Nursery and located near Fertile, Minn. The present variety was discovered in a cultivated plot of a large number of green ash seedlings grown from seed collected in northern Minnesota of the species known as *Fraxinus pennsylvanica subintegerrima.*

At the time of my discovery of the present variety, our family nursery was commercially growing many green ash seedlings. In the plot containing this variety, my attention was focused on this particular seedling, which exhibited straight rapid growth and a strong caliper, attractive bark of a bronze-tinge color, glossy narrow leaves, quick branching and upright uniform growth, and a seedless characteristic. The present variety was carefully observed for several years, and the continued observation and testing has convinced me that this seedling is a new and improved variety, as indicated by the following unique combination of outstanding qualities which distinguish this variety from all other varieties of green ash trees known to me.

SUMMARY OF CHARACTERISTICS

The unique combination of characteristics of the present variety, which has been named the Bergeson Ash, are as follows:

(1) A rapid strong growth. The variety grows approximately five feet in its fourth year, four and one-half feet in its fifth year, and three feet in subsequent years after becoming more mature. This is remarkably fast growth for the short season of northern Minnesota.

(2) The bark has an attractive bronze tinge.

(3) The tree is seedless, having only male flowers and no female flower parts.

(4) The leaves are more glossy and narrower than common varieties of green ash and remain on the tree later in the autumn.

(5) The present variety has a pronounced stronger caliper as compared with other varieties of green ash, and this characteristic is confirmed in one-year budded trees of the variety.

(6) The growth is straight and quick-branching to produce a well-formed tree.

(7) This variety tends to branch the first year of growth and needs little or no pruning or trimming when grown in the nursery for commercial sale, which is a labor-saving advantage to the grower.

(8) The upright, fast and uniform growth makes the present variety highly desirable for boulevard planting.

ASEXUAL REPRODUCTION

The present variety has been asexually reproduced by me by means of grafting at our family nursery located three miles south and five miles east of Fertile, Minn., and also by budding at Bailey Nurseries Inc., 1325 Bailey Road, Newport, Minn. Such asexual reproduction confirms the above-stated characteristics and qualities of this variety are true to form and consistent through succeeding propagation.

SUMMARY OF THE CULTIVAR

The accompanying drawings comprise photographs showing characteristics of this new variety. The photographs were taken of specimens of the variety growing in the aforesaid Bergeson Nursery at Fertile, Minn., and the color photographs depict color features as true as reasonably possible.

The following is a detailed description or specification of my new variety. Color references relate to the *Horticultural Colour Chart,* 1938 Edition, published by The British Colour Council in collaboration with The Royal Horticultural Society, London, England, except color terms of ordinary dictionary meaning as may occasionally be used.

Parentage: The present variety was produced from a seedling of an unnamed variety of the species botanically known as *Fraxinus pennsylvanica subintegerrima* raised from seed collected in northern Minnesota.

Propagation: The present variety has been asexually reproduced by budding and grafting and has held distinguishing characteristics through succeeding propagations. The locality where the present variety has been primarily grown and observed is Fertile, Minn.

Figure 2:
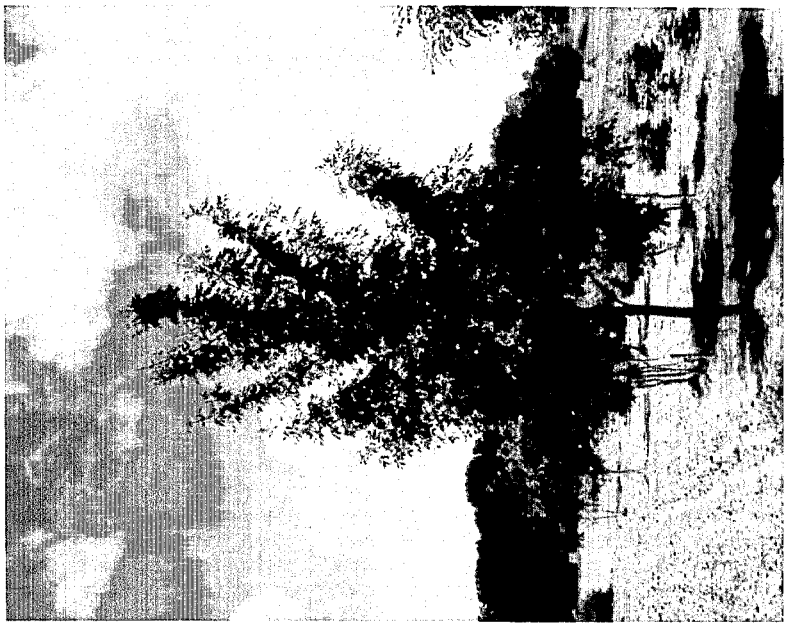
FIG. 2 is a color photograph showing the full-leaf summer form of the variety.
Figure 1:
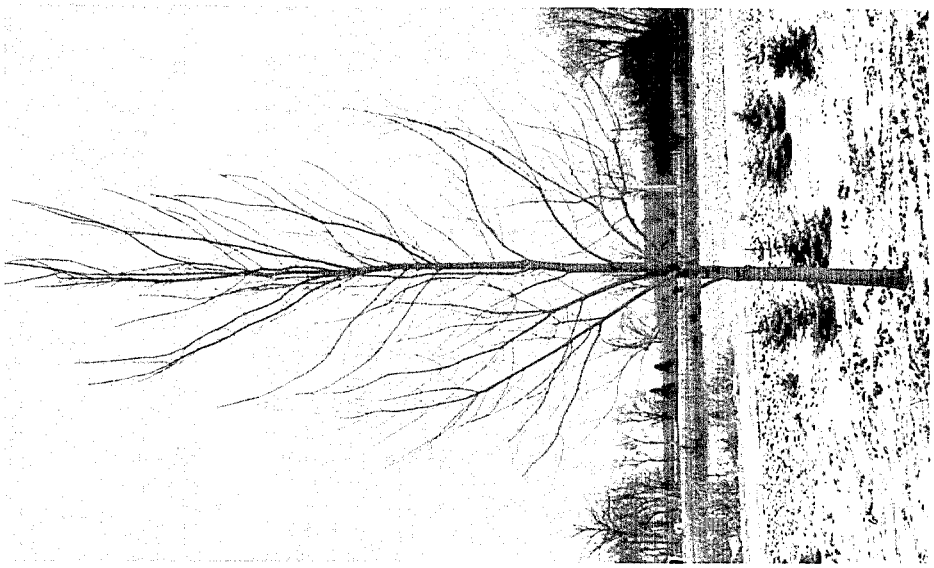
FIG. 1 is a black-and-white photograph showing the variety defoliated in winter and depicting the strong upright and branching habit of this variety.
Figure 4:
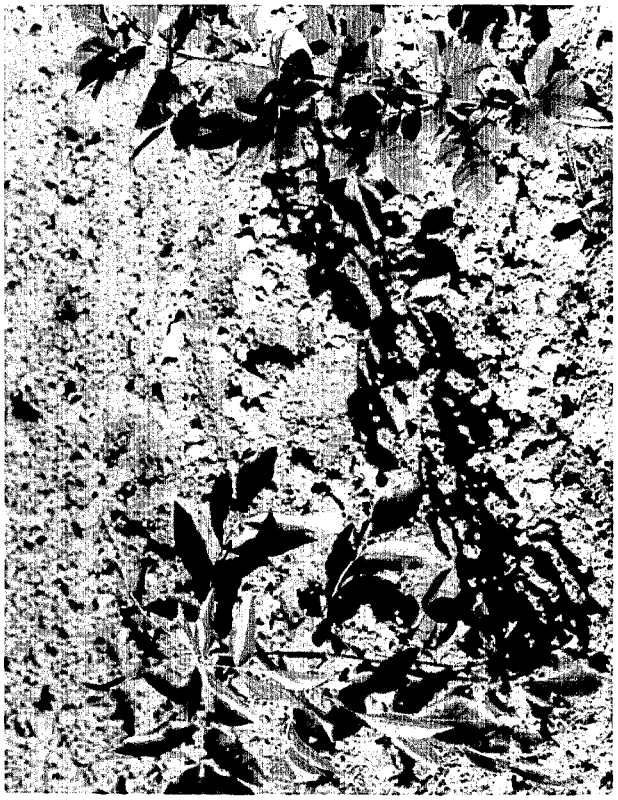
FIG. 4 is a color photograph showing a specimen of the present variety on the left with a common green ash specimen on the right, and depicting the comparatively more glossy foliage of the present variety.

Tree:

*Form.*—The present variety exhibits a form which is upright, full and well-rounded. It is faster growing than other common or commercial varieties of green ash, averaging five feet in its fourth year and four and one-half feet in its fifth year, when planted in northern Minnesota. This variety branches freely and uniformly, often branching in its first year of growth, and requires little or no pruning in the nursery to produce a well-shaped tree for commercial sale. The typical shape of this variety is illustrated in FIGS. 1 and 2.

*Trunk.*—Smooth.

*Branches.*—Smooth.

Figure 3:
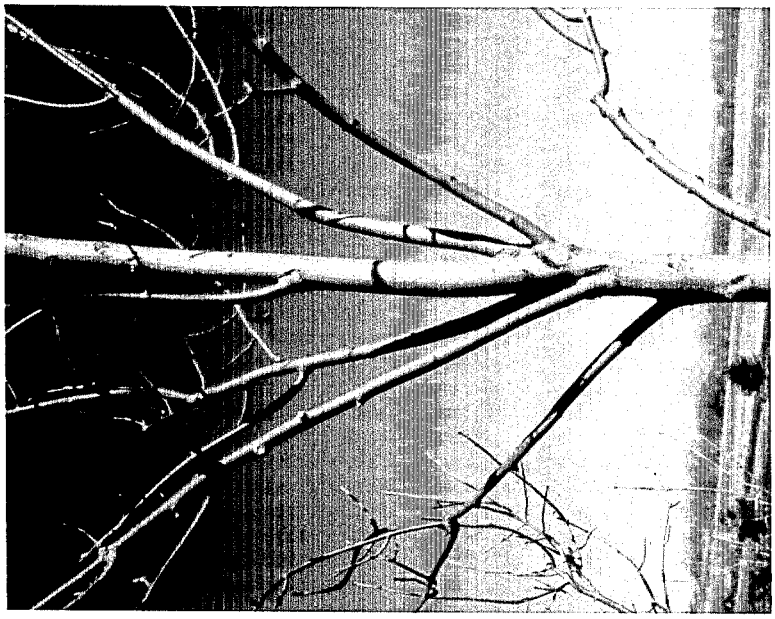
FIG. 3 is a close-up color photograph of the defoliated tree showing the bronze-tinge color of the bark.
Figure 5:
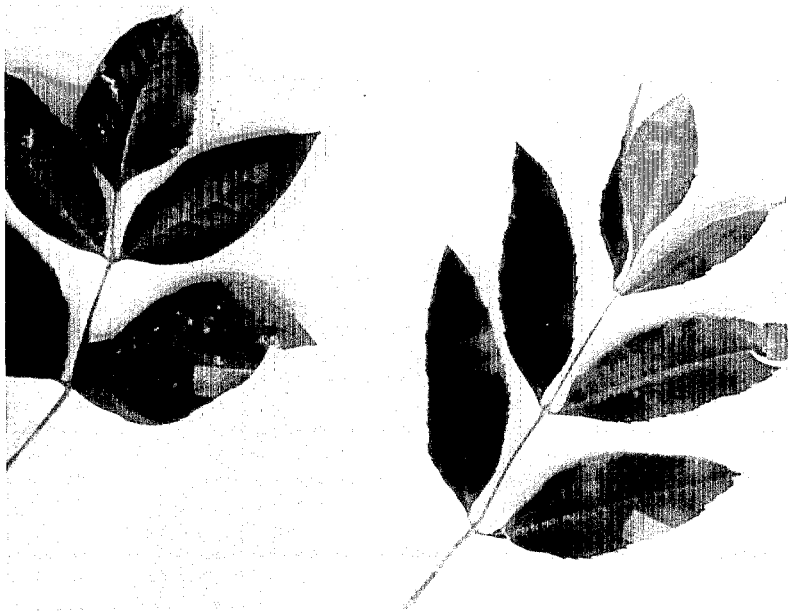
FIG. 5 is a color photograph which, although not completely true to color, shows the leaf form of the present variety on the right in comparison to the leaf form of the common green ash shown on the left.

*Bark.*—The bark on branches and trunk attains an attractive bronze color after approximately three years of age. The bronze coloring is shown in the color photograph FIG. 3, which is closely true to the actual color.

*Lenticels.*—The lenticels are circular in shape and less than the usual quantity for common and other commercial varieties of green ash.

*Leaves.*—Compound with normally 7 leaflets; from 7 to 9 inches in length overall. The leaves stay on the tree in autumn longer than other common or commercial varieties of green ash known to me.

*Leaflets.*—Length: lateral leaflets approximately $3\frac{1}{4}$ inches and terminal leaflets approximately $2\frac{3}{4}$ inches. Width: lateral leaflets approximately $1\frac{1}{4}$ inches and terminal leaflets approximately $\frac{3}{4}$ inch. Shape: narrow; ovate; pointed. Color: upper surface: Parsley Green, Color No. 00962/3 (page 193), with a high degree of gloss. Reverse: dull gray green, with no pubescence, and pronounced veins. Autumn color: becomes medium yellow as grown in northern Minnesota, similar to autumn color of Norway maple. Margin: serrate. Glands: none. Stipules: none.

*Petiole.*—Approximately two inches in length.

*Leaf buds.*—Shape: pointed; approximately 3/16 inch in diameter. Color: dusty dark brown to chocolate.

Figure 6:
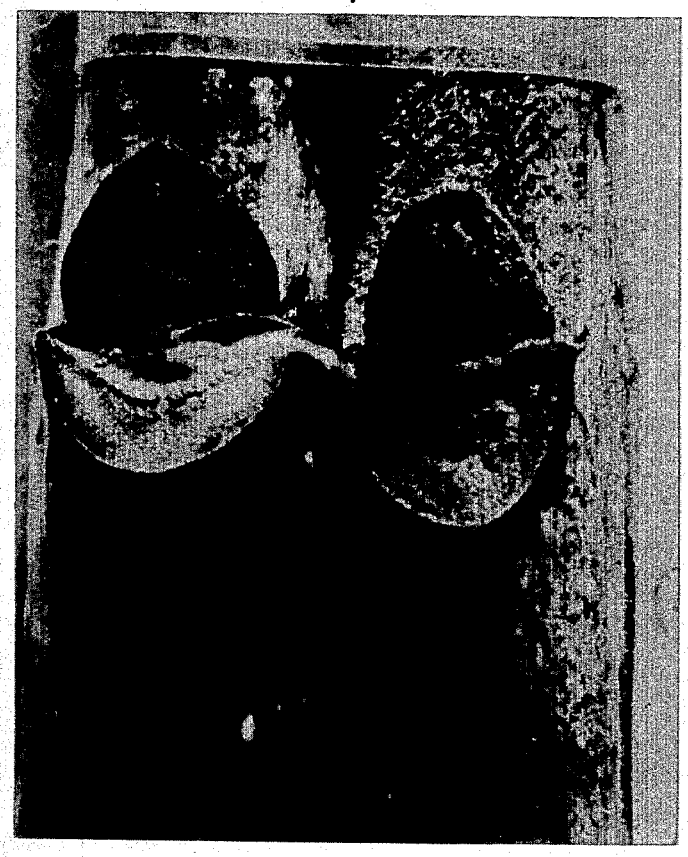
FIG. 6 is a black and white photograph showing the leaf scale scar characteristics of the present variety in comparison to the common green ash specimen shown in FIG. 4.

*Leaf scars.*—Arcuate in shape, as shown in FIG. 6.

*Flowers.*—Quantity: abundant. Size: small. Form: flowers consist of small dark brown tufts with no petals and no female flower parts. Time: blooms appear approximately May 15th as grown in northern Minnesota.

*Seeds.*—None, as determined from observation of mature tree for several years. Tree is also seedless because the variety produces only male flowers with no female flower parts.

*General characteristics.*—As compared with other common and commercial varieties of green ash trees known to me, the present variety has more rapid growth, a more attractive bronze bark color, glossier foliage which stays on the tree longer in autumn, a straight growth producing a stronger caliper, and earlier branching. Compared to such other varieties known to me, the leaves of this variety stay on the tree approximately seven days longer in the autumn. Also, this variety produces a trunk caliper which is approximately 20% larger than that of other common or commercial varieties known to me and of the same age and grown under the same conditions or in the same nursery. This variety is as winter hardy as other common and commercial varieties of green ash known to me.

I claim:

1. A new and distinct variety of green ash tree, substantially as shown and described herein, characterized particularly as to novelty by the unique combination of a rapid, straight, quick-branching, vigorous, upright, uniform and seedless growth habit which requires little or no pruning to produce a desirable nursery-grown tree for commercial sale in a minimum of growing time, with narrow glossy green leaves, an attractive bronze-color bark, a pronounced stronger caliper, a tendency to branch the first year of growth, and with leaves which stay on the tree longer in the autumn.

* * * * *

BERGESON ASH

COMMON GREEN ASH

COMMON GREEN ASH BERGESON ASH

BERGESON ASH | COMMON GREEN ASH